US012153028B2

(12) United States Patent
Wang et al.

(10) Patent No.: US 12,153,028 B2
(45) Date of Patent: Nov. 26, 2024

(54) CHROMATOGRAPHIC ANALYSIS SYSTEM, CHROMATOGRAM DETECTION AND ANALYSIS METHOD AND ELECTRONIC DEVICE

(71) Applicant: Acchrom Tech (Dalian) Technology Co., Ltd, Liaoning (CN)

(72) Inventors: Dongqiang Wang, Dalian (CN); Yuzhang Ji, Dalian (CN)

(73) Assignee: ACCHROM TECHNOLOGIES CO., LTD., Beijing (CN)

( * ) Notice: Subject to any disclaimer, the term of this patent is extended or adjusted under 35 U.S.C. 154(b) by 329 days.

(21) Appl. No.: 17/640,767

(22) PCT Filed: Feb. 18, 2022

(86) PCT No.: PCT/CN2022/076808
§ 371 (c)(1),
(2) Date: Mar. 4, 2022

(87) PCT Pub. No.: WO2022/179444
PCT Pub. Date: Sep. 1, 2022

(65) Prior Publication Data
US 2023/0152286 A1 May 18, 2023

(30) Foreign Application Priority Data

Feb. 25, 2021 (CN) .......................... 202110208286.2
Jul. 22, 2021 (CN) .......................... 202110830533.2
Jul. 22, 2021 (CN) .......................... 202110830534.7

(51) Int. Cl.
G01N 30/86 (2006.01)
G16C 20/62 (2019.01)

(52) U.S. Cl.
CPC ..... *G01N 30/8651* (2013.01); *G01N 30/8627* (2013.01); *G01N 30/8631* (2013.01); *G16C 20/62* (2019.02)

(58) Field of Classification Search
None
See application file for complete search history.

(56) References Cited

U.S. PATENT DOCUMENTS 6,971,059 B1 * 11/2005 Knipe, Jr. .......... G01N 30/8651
715/205
8,428,889 B2 * 4/2013 Wright ............... G01N 30/8624
702/32

(Continued)

FOREIGN PATENT DOCUMENTS

CN 104297504 A * 1/2015
CN 109870515 A * 6/2019
DE 102017126893 A * 5/2019 ............. G01N 30/32

*Primary Examiner* — Daniel S Larkin
(74) *Attorney, Agent, or Firm* — Chun-Ming Shih; LANWAY IPR SERVICES

(57) ABSTRACT

The present disclosure relates to a chromatographic analysis system, a chromatogram detection and analysis method and an electronic device, belonging to that technical field of chromatographic analysis, wherein the system comprises a data acquiring unit, which is configured to acquire raw data generated by a chromatographic analysis instrument; an analysis processing unit, which is configured to analyze the raw data based on the analysis operation configured by a user to obtain analysis data; a storing and managing unit, which is configured to store raw data and analysis data, and store method parameters and management data of the analysis system; a client unit, which is configured to provide the interactive interface of the system to a user; wherein the storing and managing unit comprises a first database for storing raw data and analysis data and a second database for storing method parameters and management data of the (Continued)

analysis system. The present disclosure is beneficial to ensuring the integrity and security of the acquired raw data and meeting the new demands in the industry practice.

7 Claims, 12 Drawing Sheets

(56) References Cited

U.S. PATENT DOCUMENTS

| | | | | |
|---|---|---|---|---|
| 2014/0088923 | A1* | 3/2014 | Wang | H01J 49/0036 702/191 |
| 2015/0276691 | A1* | 10/2015 | Foley | B01D 15/10 73/23.35 |

* cited by examiner

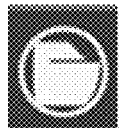
FIG. 4

Comparing the slope of each point on the chromatographic curve with a threshold, and determining the reference point of the chromatographic peak based on the comparison result, wherein the reference point comprises a reference point of a peak starting point, a reference point of a temporary peak point, and a reference point of a peak end point — S121

Based on the position of the chromatographic peak characterized by the reference point on the chromatographic curve, pattern recognition detection is performed on the chromatographic curve near the position with a Gaussian wave as a matching wave, and the peak point in the recognition detection result is taken as the correction point of the peak point — S122

Correction processing is performed on the reference point of the temporary peak point according to the correction point of the peak point, and the corrected point is taken as the reference point of the peak point — S123

Chromatographic peaks characterized by the reference point of the peak starting point, the reference point of the peak end point and the reference point of the peak point are determined as detected chromatographic peaks — S124

FIG. 9

CHROMATOGRAPHIC ANALYSIS SYSTEM, CHROMATOGRAM DETECTION AND ANALYSIS METHOD AND ELECTRONIC DEVICE

TECHNICAL FIELD

The present disclosure belongs to the technical field of chromatographic analysis, and in particular relates to a chromatographic analysis system, a chromatogram detection and analysis method, and an electronic device.

BACKGROUND

As a branch of chemistry field, chromatography is mainly used to separate and purify some mixed substances. With the continuous development of science and technology, there are some related analysis instruments and devices, such as liquid chromatograph or gas chromatograph or ion chromatograph, which we often mention. These instruments and devices only separate different kinds of substances and state of substances, and their principles are based on chromatographic theory.

In practice, after the mixture is separated, it involves data acquisition and data analysis. However, in some scenarios where chromatographic analysis is applied (such as pharmaceuticals, etc.), it will involve the need of data review in the industry, it is necessary to analyze relevant data and issue corresponding reports, and government departments or corresponding regulatory authorities need to inspect the integrity of data, which puts forward new requirements for data management in the chromatographic analysis process. The existing chromatographic workstation system cannot meet this requirement.

At the same time, in related technologies, qualitative and quantitative analysis of chromatograms should be carried out by computer in chromatographic analysis, in which the important basis of analysis is to identify chromatographic peaks. The peak types of the chromatographic peaks are complex and diverse, including overlapping peaks, front shoulder peaks, back shoulder peaks, tail peaks and negative peaks, etc.

At present, a time window method and a derivative method are generally used to detect and identify chromatographic peaks. The time window method obtains the chromatographic peak position by finding the extreme value in the retention time range of components. The derivative method obtains a series of extreme values by obtaining the derivative of the original chromatographic data, and then finds the chromatographic peak position according to the retention time range of components.

In the process of realizing the time window method and the derivative method, it is necessary to combine the amplitude threshold to determine whether it is the real chromatographic peak. Therefore, whether the threshold is set reasonably is very important. If the threshold is set to be too large, the real chromatographic peak may be missed, which reduces the resolution of chromatographic components. If it is set to be too small, some small peaks formed by noise will be regarded as chromatographic peaks, which will lead to misjudgment. Moreover, both the time window method and the derivative method need the retention time range of components to find the chromatographic peak position. Therefore, if the peak drifts out of this range, it will lead to the problem of incorrect chromatographic peak or misjudgment of components. In addition, using the method of combining the first derivative and the second derivative to find chromatographic peak has a high recognition rate for a single peak, but the recognition rate will be greatly reduced when there are multiple peaks overlapping, especially when shoulder peaks appear.

In related technologies, there is a method to identify chromatographic peaks based on pattern matching, which has nothing to do with the retention time of chromatographic components when identifying peaks, and is insensitive to noise and changes in the width and amplitude of the chromatographic peaks. However, this algorithm uses the statistical method of the correlation coefficient to calculate the similarity between the matched waveform and the chromatographic curve. Therefore, the threshold setting of the correlation degree is very important, which will lead to poor universality of the pattern matching method.

The above content is only used to help understand the technical scheme of the present disclosure, and does not mean admitting that the above content is the prior art.

SUMMARY

In order to overcome the problems in related technologies at least to a certain extent, the present disclosure provides a chromatographic analysis system based on a dual-database architecture, which uses a separate database to store and manage the acquired raw data, which is beneficial to ensuring the integrity and security of the acquired raw data and meeting the new demands in the industry practice.

To achieve the above purpose, the present disclosure uses the following technical scheme.

In a first aspect,
the present disclosure provides a chromatographic analysis system based on a dual-database architecture, comprising:
a data acquiring unit, which is configured to acquire raw data generated by a chromatographic analysis instrument;
an analysis processing unit, which is configured to analyze the raw data based on the analysis operation configured by a user to obtain analysis data;
a storing and managing unit, which is configured to store raw data and analysis data, and store method parameters and management data of the analysis system;
a client unit, which is configured to provide the interactive interface of the system to a user;
wherein the storing and managing unit comprises a first database for storing raw data and analysis data and a second database for storing method parameters and management data of the analysis system.

Preferably, a standard method library, a typical item library and a user method library are built in the second database;
the standard method library integrates a plurality of traditional Chinese medicine analysis methods, which are established based on the separation requirements and a content analysis method of corresponding traditional Chinese medicine in pharmacopoeia;
the typical item library is configured to store commonly used detection items in the field, and the detection items comprise analysis methods and spectrogram data corresponding to corresponding items;
the user method library is configured to store the analysis methods established by a user, which facilitates the reuse of the analysis methods.

Preferably, the typical item library stores one-click detection items;

sample configuration requirements, instruments and operation requirements, analysis method configuration and analysis report templates are built in the one-click detection items, which is convenient for a user to call the item for one-click detection and analysis operation through an interactive interface.

Preferably, the storing and managing unit further comprises a second database managing module;

the second database managing module is configured to realize an implantation and deletion function, an authorization management function, an item locking and unlocking function, and a check-in and check-out function of online users of items.

Preferably, the chromatographic analysis system further comprises an intelligent auxiliary unit, wherein the intelligent auxiliary unit comprises an intelligent diagnosis module;

the intelligent diagnosis module is configured to automatically analyze and diagnose instrument faults, generate diagnosis reports and solution suggestions, so as to help users troubleshoot.

Preferably, the intelligent auxiliary unit further comprises an intelligent chromatographic expert system module;

the intelligent chromatographic expert system module is configured to assist users in method development and realize method recommendation and intelligent method matching functions.

Preferably, the intelligent chromatographic expert system module comprises:

a method intelligent recommendation sub-module, which is configured to perform intelligent diagnosis and parameter recommending on the set method parameters when the user establishes an analysis method;

an application knowledge base sub-module, which has the industry standard data, national standards and pharmacopoeia method data used in the industry built therein, and is configured to provide the user with a local knowledge base query function;

an intelligent interaction sub-module, which is configured to push a relevant auxiliary prompt to a user when the user performs interactive operation;

a gradient method optimization sub-module, which is configured to provide gradient optimization method suggestions to a user when the analysis results are not satisfactory.

Preferably, the chromatographic analysis system further comprises a Web server unit, which is configured to provide the interactive interface of the system to a user in the form of browser pages.

Preferably, both the first database and the second database are deployed in the cloud.

Preferably, the first database uses MongoDB database system, and the second database uses Mysql database system.

In a second aspect, the present disclosure provides a chromatogram detection and analysis method, comprising:

acquiring original spectrogram data to be processed, and performing noise reduction processing on the original spectrogram data to obtain de-noising spectrogram data;

calculating the curvature of each point on the chromatographic curve based on the original spectrogram data, and determining the point on the chromatographic curve whose curvature value is greater than a first threshold as a temporary peak point, wherein the first threshold is determined based on the calculation and analysis of a no-load output signal of a chromatographic instrument generating the original spectrogram data;

performing pattern recognition detection on the de-noising spectrogram data by using a Gaussian wave as a matching wave, and taking the peak point in the recognition detection result as the reference point of the peak point;

performing pairwise corresponding comparison between each temporary peak point and each reference point of the peak point, and determining the point with a larger ordinate value as the peak point;

for the chromatographic curve corresponding to the de-noising spectrogram data, starting from each peak point on the curve, performing point-by-point extended detection to both sides of the corresponding peak point, respectively, and determining the peak starting point and the peak end point corresponding to the corresponding peak point according to the curvature of each point in the detection process;

taking chromatographic peaks characterized by each peak point and its corresponding peak starting point and peak end point as detected chromatographic peaks, and generating detection results based on the detected chromatographic peaks.

Preferably, the calculation and analysis process of a no-load output signal of a chromatographic instrument generating the original spectrogram data comprises:

performing statistical analysis on the slope change of the output baseline of the chromatographic instrument when it is unloaded, calculating the variance of the slope change, and then determining the standard deviation of the slope change;

taking the standard deviation of the slope change of a preset multiple as the first threshold.

Preferably, the point-by-point extended detection comprises the following processing steps for each peak point:

determining curvature inflection points on both sides of the peak point;

performing point-by-point detection on the left side with the curvature inflection point on the left side of the peak point as the base point, when the curvature of a point is less than a second threshold and the curvature of the point before the point is greater than the second threshold, comparing the ordinate values of the two points, and determining the point with a smaller ordinate value as the peak starting point corresponding to the peak point;

performing point-by-point detection on the right side with the curvature inflection point on the right side of the peak point as the base point, when the curvature of a point is less than a third threshold and the curvature of the point before the point is greater than the third threshold, comparing the ordinate values of the two points, and determining the point with a smaller ordinate value as the peak end point corresponding to the peak point.

Preferably, the second threshold and the third threshold are configured and determined based on the values input by the user, and their default values are zero when there is no user input.

Preferably, performing pattern recognition detection on the de-noising spectrogram data by using a Gaussian wave as a matching wave and taking the peak point in the recognition detection result as the reference point of the peak point comprises:

taking the chromatographic curve corresponding to the de-noising spectrogram data as the curve to be detected, sliding the waveform of the Gaussian wave from the left end point to the right end point on the curve to be detected and simultaneously calculating the correlation coefficients, and obtaining the correlation coefficient group of the chromatographic data of the curve to be detected relative to the Gaussian wave based on the calculation result;

comparing and analyzing each correlation coefficient in the correlation coefficient group with a predetermined value, determining the peak position of the Gaussian wave based on the correlation coefficient whose coefficient value is greater than the predetermined value, and determining the point at this position on the curve to be detected as the reference point of the peak point.

Preferably, generating the detection result based on the detected chromatographic peak comprises:

integrating the detected chromatographic peak, and calculating and determining the area and height of the chromatographic peak.

Preferably, the detection and analysis method further comprises:

performing detection processing on the original spectrogram data using a reference chromatogram detection algorithm to obtain a reference detection result;

comparing and analyzing the detection result with the reference detection result, generating a detection evaluation report, and displaying and outputting the detection evaluation report.

Preferably, comparing and analyzing the detection result with the reference detection result comprises:

matching the detected chromatographic peaks in the detection result and the reference detection result, determining the matched chromatographic peaks, and generating a detection evaluation report based on the proportion of the matched chromatographic peaks in the detected chromatographic peaks and the difference of the matched chromatographic peaks.

In a third aspect, the present disclosure provides a chromatogram detection and analysis method, comprising:

acquiring original spectrogram data to be processed;

for the original spectrogram data, using a time window of preset size to sequentially slide from the starting point of the chromatogram curve to perform the detection processing of chromatogram peaks until the original spectrogram data is processed, detecting all chromatogram peaks in the curve, and generating a detection result based on the detected chromatogram peaks;

wherein the detection process of each chromatographic peak comprises:

comparing the slope of each point on the chromatographic curve with a threshold, and determining the reference point of the chromatographic peak based on the comparison result, wherein the reference point comprises a reference point of a peak starting point, a reference point of a temporary peak point, and a reference point of a peak end point, and the threshold is determined based on the calculation and analysis of the no-load output signal of the chromatographic instrument generating the original spectrogram data;

based on the position of the chromatographic peak characterized by the reference point on the chromatographic curve, performing pattern recognition detection on the chromatographic curve near the position with a Gaussian wave as a matching wave, and taking the peak point in the recognition detection result as the correction point of the peak point;

performing correction processing on the reference point of the temporary peak point according to the correction point of the peak point, and taking the corrected point as the reference point of the peak point;

determining chromatographic peaks characterized by the reference point of the peak starting point, the reference point of the peak end point and the reference point of the peak point as detected chromatographic peaks.

Preferably, comparing the slope of each point on the chromatographic curve with a threshold and determining the reference point of the chromatographic peak based on the comparison result comprises:

calculating the slope of the points on the chromatographic curve in the sliding process of the time window in real time, comparing the calculated slope with a predetermined fourth threshold, comparing the ordinate values of the two points when the slope of two consecutive points is greater than the fourth threshold, and determining the point with a smaller ordinate value as the reference point of the peak starting point, and analyzing and judging the positive and negative change of the slope of the point after the reference point of the peak starting point, comparing the ordinate values of the two points when the slope of one point is negative and the slope of the point before the point is positive, and determining the point with a larger ordinate value as the reference point of the temporary peak point, and comparing the slope of the point after the reference point of the temporary peak point with a predetermined fifth threshold, comparing the ordinate values of the two points when the slope of two consecutive points is less than the fifth threshold, and determining the point with a smaller ordinate value as the reference point of the peak end point.

Preferably, the calculation and analysis process of a no-load output signal of a chromatographic instrument generating the original spectrogram data comprises:

performing statistical analysis on the slope change of the output baseline of the chromatographic instrument when it is unloaded, calculating and determining the variance of the slope change, and then determining the standard deviation of the slope change;

taking the standard deviation of the slope change of three times as the fourth threshold, and taking the standard deviation of the slope change of negative three times as the fifth threshold.

Preferably, performing correction processing on the reference point of the temporary peak point according to the correction point of the peak point and taking the corrected point as the reference point of the peak point specifically comprises:

comparing the ordinate values of the correction point of the peak point and the reference point of the temporary peak point, and determining the point with a larger ordinate value as the reference point of the peak point.

Preferably, performing pattern recognition detection on the chromatographic curve near the position with a Gaussian wave as a matching wave and taking the peak point in the recognition detection result as the correction point of the peak point comprises:

taking the chromatographic curve near the position as the curve to be detected, sliding the waveform of the Gaussian wave from the left end point to the right end point on the curve to be detected and simultaneously calculating the correlation coefficients, and obtaining the correlation coefficient group of the chromatographic data of the curve to be detected relative to the Gaussian wave based on the calculation result;

comparing and analyzing each correlation coefficient in the correlation coefficient group with a predetermined value, determining the peak position of the Gaussian wave based on the correlation coefficient whose coefficient value is greater than the predetermined value, and determining the point at this position on the curve to be detected as the correction point of the peak point.

Preferably, generating the detection result based on the detected chromatographic peak comprises:

integrating the detected chromatographic peak, and calculating and determining the area and height of the chromatographic peak.

Preferably, the detection and analysis method further comprises:

performing detection processing on the original spectrogram data using a reference chromatogram detection algorithm to obtain a reference detection result;

comparing and analyzing the detection result with the reference detection result, generating a detection evaluation report, and displaying and outputting the detection evaluation report.

Preferably, comparing and analyzing the detection result with the reference detection result comprises:

matching the detected chromatographic peaks in the detection result and the reference detection result, determining the matched chromatographic peaks, and generating a detection evaluation report based on the proportion of the matched chromatographic peaks in the detected chromatographic peaks and the difference of the matched chromatographic peaks.

In a fourth aspect, the present disclosure provides an electronic device, comprising:

a memory on which an executable program is stored;

a processor which is configured to execute the executable program in the memory to realize the steps of the method described above.

By using the above technical scheme, the present disclosure has at least the following beneficial effects.

In the chromatographic analysis system, a dual-database architecture is used, and the acquired raw data is stored and managed in a separate database, which is beneficial to ensuring the integrity and security of the acquired raw data and meeting the new demands of the industry practice (demands such as electronic approval and data security). Based on pattern matching and in conjunction with the curvature of the chromatographic curve, the liquid and gas chromatograms are actually detected, which improves the reliability of detection as a whole. In addition, the threshold in the curvature detection method is automatically calculated and determined based on the signal of the instrument itself, and the peak feature points detected by pattern matching are only used as reference points to correct the peak feature points obtained based on curvature detection, which also makes up for the defects of the two methods in the prior art.

Other advantages, objectives, and features of the present disclosure will be set forth in the following description to some extent, and to some extent, it will be obvious to those skilled in the art based on the following investigation and study, or it may be learned from the practice of the present disclosure. The objectives and other advantages of the present disclosure can be realized and obtained by the structure particularly pointed out in the following description, claims and drawings.

BRIEF DESCRIPTION OF THE DRAWINGS

The drawings are used to provide a further understanding of the technical scheme of the present disclosure or the prior art and form a part of the specification. The drawings expressing the embodiments of the present disclosure together with the embodiments of the present disclosure are used to explain the technical scheme of the present disclosure, but do not constitute a limitation on the technical scheme of the present disclosure.

FIG. 4 is a schematic diagram illustrating an interactive interface of one-click detection according to an embodiment of the present disclosure.

FIG. 9 is a schematic flow diagram of a chromatographic peak detection according to the embodiment shown in FIG. 8.

DETAILED DESCRIPTION OF THE EMBODIMENTS

In order to make the purpose, technical scheme and advantages of the present disclosure clearer, the technical scheme of the present disclosure will be described in detail hereinafter. Obviously, the described embodiments are only part of the embodiments of the present disclosure, rather than all of the embodiments. Based on the embodiments in the present disclosure, all other embodiments obtained by those skilled in the art without paying creative labor fall within the scope of protection of the present disclosure.

Embodiment 1

In the development of chromatographic science, with the development of analysis instruments, the supporting software is constantly updated. The supporting software here is generally referred to as chromatographic workstation, which is equivalent to an upper computer. On the one hand, the lower computer (such as a liquid chromatography system device) is controlled, and on the other hand, the chromatographic data acquired by the lower computer is analyzed and processed, so as to analyze the samples to be detected.

The original chromatographic workstation is a stand-alone workstation (a workstation installed in a computer, which is dedicated to controlling an instrument and equivalent to being dedicated to a special computer). Later, a network workstation is developed, in which the instruments used were connected to several acquisition servers. One acquisition server can be connected to a single instrument or multiple instruments for data acquisition, and then the client can be used for instrument acquisition control, analysis and processing operations.

In the software system of stand-alone version, files and data related to the items are generally stored in the form of folders, and users can delete them directly, which has hidden dangers in data security and integrity. However, the existing workstations using database use a single database system, and relevant personnel save the system parameter data in the database. However, the acquired raw data are still saved in the form of files, that is, there are still hidden dangers in data security and integrity.

As mentioned in the background, with the industry-related practitioners and reviewers paying more and more attention to data security, the problems of data management in the existing chromatographic workstation system become more and more prominent. In view of this, the present disclosure proposes a chromatographic analysis system based on a dual-database architecture.

Figure 1:
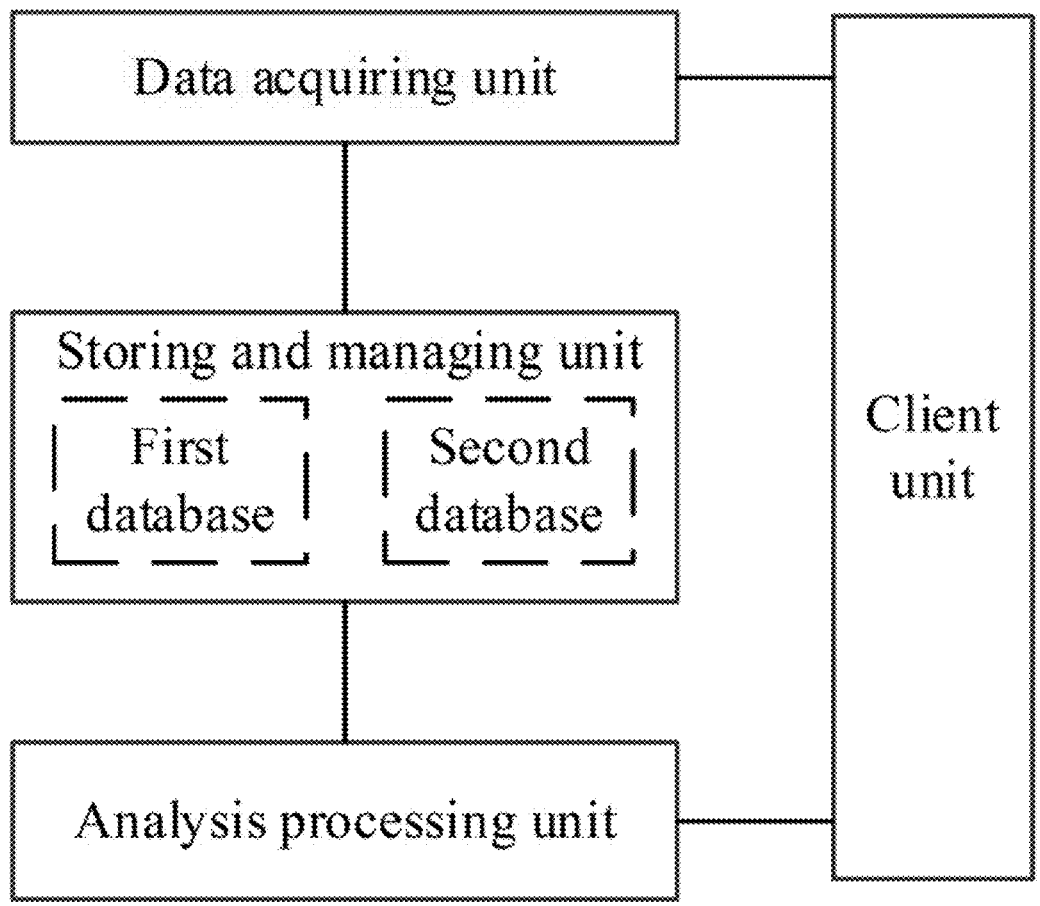
FIG. 1 is a schematic diagram of a system structure of a chromatographic analysis system with a dual-database architecture according to an embodiment of the present disclosure.

In one embodiment, as shown in FIG. 1, the chromatographic analysis system based on a dual-database architecture comprises:

- a data acquiring unit, which is configured to acquire raw data generated by a chromatographic analysis instrument;
- an analysis processing unit, which is configured to analyze the raw data based on the analysis operation configured by a user to obtain analysis data;
- a storing and managing unit, which is configured to store raw data and analysis data, and store method parameters and management data of the analysis system.

As shown in FIG. 1, the storing and managing unit here comprises a first database for storing raw data and analysis data and a second database for storing method parameters and management data of the analysis system. The system further comprises a client unit, which is configured to provide the interactive interface of the system to a user.

According to the technical scheme of the present disclosure, in the chromatographic analysis system, the dual-database architecture is used, and the acquired raw data is stored and managed by a separate database, which is beneficial to ensuring the integrity and security of the acquired raw data and meeting the new demands in the industry practice.

Further, as a specific embodiment, the system further comprises a Web server unit, which is configured to provide the interactive interface of the system to a user in the form of browser pages. That is, in this embodiment, related network technologies are used based on a BS architecture, which solves the problems of remote transmission and processing, and realizes the remote control and application of the chromatographic analysis system.

As a specific embodiment, databases can be deployed locally. Specifically, the first database can use MongoDB database system, and the second database can use Mysql database system. As another specific embodiment, both the first database and the second database are deployed in the cloud. Based on cloud technology, compared with the local deployment database, the storage, backup and sharing of related data can be better realized.

Figure 2:
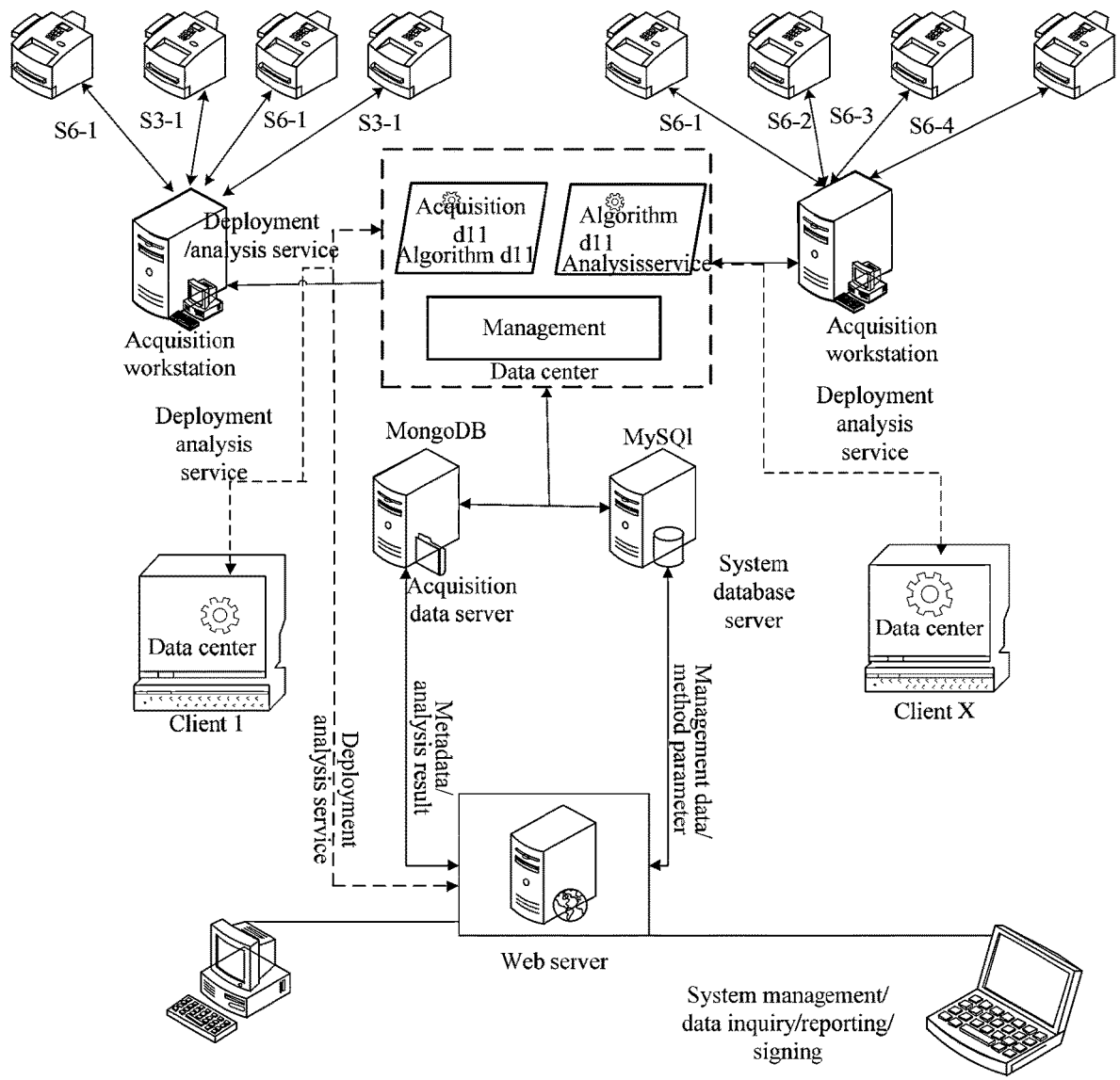
FIG. 2 is a schematic diagram of the application of a chromatographic analysis system with a dual-database architecture according to an embodiment of the present disclosure.

For example, FIG. 2 is a schematic diagram of the application of a chromatographic analysis system in one embodiment.

As shown in FIG. 2, each acquisition workstation is connected with multiple chromatographic analysis instruments (S3-1, S6-1, etc. in the figure). The acquisition workstations in the figure are not limited to two. The number of acquisition servers is related to the number of connected instruments. The more instruments are connected, the more acquisition workstations are needed (for example, one acquisition workstation can be connected to control up to four liquid chromatography systems. If there are more than 20 workstations designed and configured in the whole system, more than 200 liquid chromatography systems can be supported).

In FIG. 2, the data center and the client are software functional entities in the system, which can be deployed in corresponding computing devices. From the data flow point of view, the client issues the acquisition related instructions, the acquisition service of the data center operates, controls the acquisition workstation to acquire the data generated by the instrument, and stores the acquired data generated by the operation of the instrument in the acquisition data server (where the first database is deployed) and the system database server (where the second database is deployed), respectively.

After the acquisition is completed, the analysis operation is carried out, the client sends analysis related instructions, the analysis service of the data center operates, the database is accessed, the analysis service is carried out based on the analysis algorithm, and the obtained analysis data is saved in the first database.

In FIG. 2, the MongoDB database system deployed on the acquisition data server mainly stores the processing raw data and data analysis results, while the Mysql database system deployed on the system database server mainly stores the processing management data and method parameters, which are not synchronized but related. MongoDB is a non-relational data database. Using this database in storing raw data can solve the problems of slow query and poor efficiency of high-frequency reading and writing when the traditional relational database processes a large amount of data. Mysql is a relational database, which can greatly reduce the probability of data redundancy and data inconsistency and ensure data integrity when storing method parameters and data management parameters.

The technical scheme of the present disclosure is equivalent to adding a database system on the basis of the original single database system in the market, the purpose of which is to make up for the defect that the existing single database only stores method parameters/management data.

As shown in FIG. 2, the embodiment shown in FIG. 2 further comprises a Web server, which is configured to provide related web page access services and realize the functions of system management, data query, report, signing and the like through the browser terminal.

On the other hand, with the development of the industry, new requirements are put forward for the operation and management function, interaction friendliness and intelligence of the chromatographic software system. In view of this, the chromatographic analysis system based on the dual-database architecture in the technical scheme of the present disclosure has also been improved in this aspect.

First of all, consider the convenience and universality of use. The difficulty of analysis and detection operation is the establishment of the analysis method. Once a stable analysis method is established, the detection operation is more of a process operation of repeated detection. At the same time, in some fields, such as some third-party testing institutions, QC laboratories, etc., there is less research and development. There is more detection with reference to pharmacopoeia and national standards, and the analysis and detection work is basically repeated operation. The repeated operation here mainly refers to that the set sequence, operation method, data processing and reporting requirements are all consistent, but different batches of samples need to be detected.

In an embodiment, in order to improve the convenience and universality of the chromatographic analysis system, the present disclosure has a built-in typical method library in the system (the typical method library here is from the view of the analysis method dimension).

In the present disclosure, the second database is configured to store the method parameters and management data of the analysis system. Specifically, in this embodiment, a standard method library, a typical item library and a user method library are built in the second database (all of them belong to the typical method library from the view of the analysis method dimension).

As the precious wealth of the Chinese nation, the separation and analysis of traditional Chinese medicine has always been the focus and difficulty of research, and the foundation and source of the related analysis methods of traditional Chinese medicine is Pharmacopoeia. In view of this, in this embodiment, the standard method library integrates a plurality of traditional Chinese medicine analysis methods, which are established based on the separation requirements and a content analysis method of corresponding traditional Chinese medicine in pharmacopoeia. It is easy to understand that the standard method library can also integrate analysis methods in food, medicine, environment and other fields.

The user method library, which is similar to the existing software, is configured to store the analysis methods established by a user, which facilitates the reuse of the analysis methods and the storage of method related data.

The typical item library, which is mainly set up for commonly used detection items in the field, is configured to store commonly used detection items in the field, and the detection items comprise analysis methods and spectrogram data corresponding to corresponding items. It is easy to understand that the specific composition of the typical item library can be configured according to the demands of the customers themselves, and in practice, the data related to customers can be packaged into the database in a customized way.

In addition, similar to the prior art, in this embodiment, the second database further comprises a spectral library to realize purity analysis of the detected samples.

Further, as a specific embodiment, the typical item library further stores one-click detection items; sample configuration requirements, instruments and operation requirements, analysis method configuration and analysis report templates are built in the one-click detection items, which is convenient for a user to call the item for one-click detection and analysis operation through an interactive interface.

The implementation of one-click detection is introduced hereinafter.

The sources of one-click detection items include two aspects. First, the items obtained by building the pharmacopoeia method, the industry standard detection method and the national standard detection method in related items. For example, based on the methods in Pharmacopoeia, a large number of experiments are carried out. Related information such as sample configuration requirements, instrument and operation requirements, analysis method configuration (the analysis method, the sequence table, the processing method), analysis report templates and so on are summarized, and these information is integrated and packaged to obtain the required items. Based on the demands of customers, matching items are established, and one-click detection customized items are launched and are build therein based on the demands of customers themselves.

Figure 3:
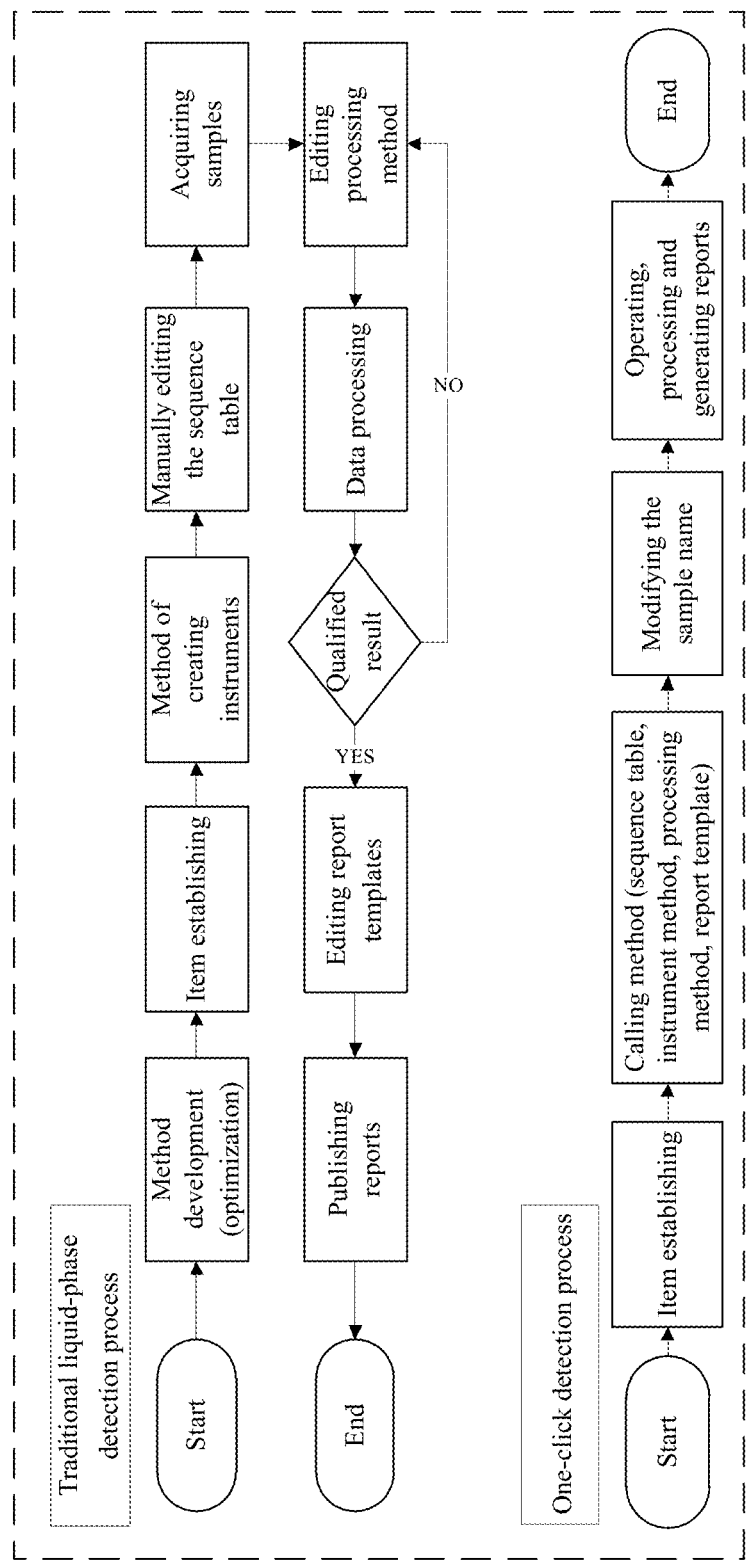
FIG. 3 is a schematic diagram illustrating the process comparison between one-click detection and traditional detection according to an embodiment of the present disclosure.

However, in practical application, one-click detection can be realized by calling one-click detection items. Compared with traditional detection, from the user's point of view, a part of the operations of developing methods, analyzing data and issuing reports are omitted. The specific omitted parts are shown in FIG. 3, and the dark process steps in the process shown in the upper part of FIG. 3 are equivalent to being omitted for users.

FIG. 4 is a schematic diagram of an interactive operation interface for one-click detection in an embodiment. In practical operation, the operator selects the item and calls the item to be executed in the interface shown in FIG. 4. According to the sample placement prompt, the samples are placed according to the identification of the sample plate, that is, the standard samples are placed at the places marked with standard samples and the unknown samples are placed at the places marked with unknown samples; then starting detection is clicked, and the system will automatically detect the samples, generate and issue the detection report in the specified format.

In order to facilitate the management and configuration of the second database, the storing and managing unit further comprises a second database managing module; the second database managing module is configured to realize an implantation and deletion function, an authorization management function, an item locking and unlocking function, and a check-in and check-out function of online users of items.

Specifically, the implantation function in the second database managing module mainly refers to the fact that in the initial software installation period, the software installation engineer implants the required methods into the database according to the demands of users.

The authorization management function mainly involves the allocation of authorization, that is, which users or user groups can call the methods in the database, and what operations authorized users can perform on the database, etc.

For the item locking and unlocking function, both locking and unlocking are for the detected items. For example, if this function is used to set item X to the locked state for user a and user group A, the operating authority of user a and user group A for item X will change, and user group A and user a only have the authority to view, but have no authority to modify and process data. For user b and user group B, item X is set to the unlocked state, and user b and user group B can view and process the data for the unlocked item.

The deletion function is mainly used to delete analysis methods and detection items in the database.

The check-in and check-out function of online users of items is used to limit the number of users online, ensuring that a single user can perform data acquisition and data processing operations on the detected items online, and avoiding data confusion caused by multi-user operations.

Figure 5:
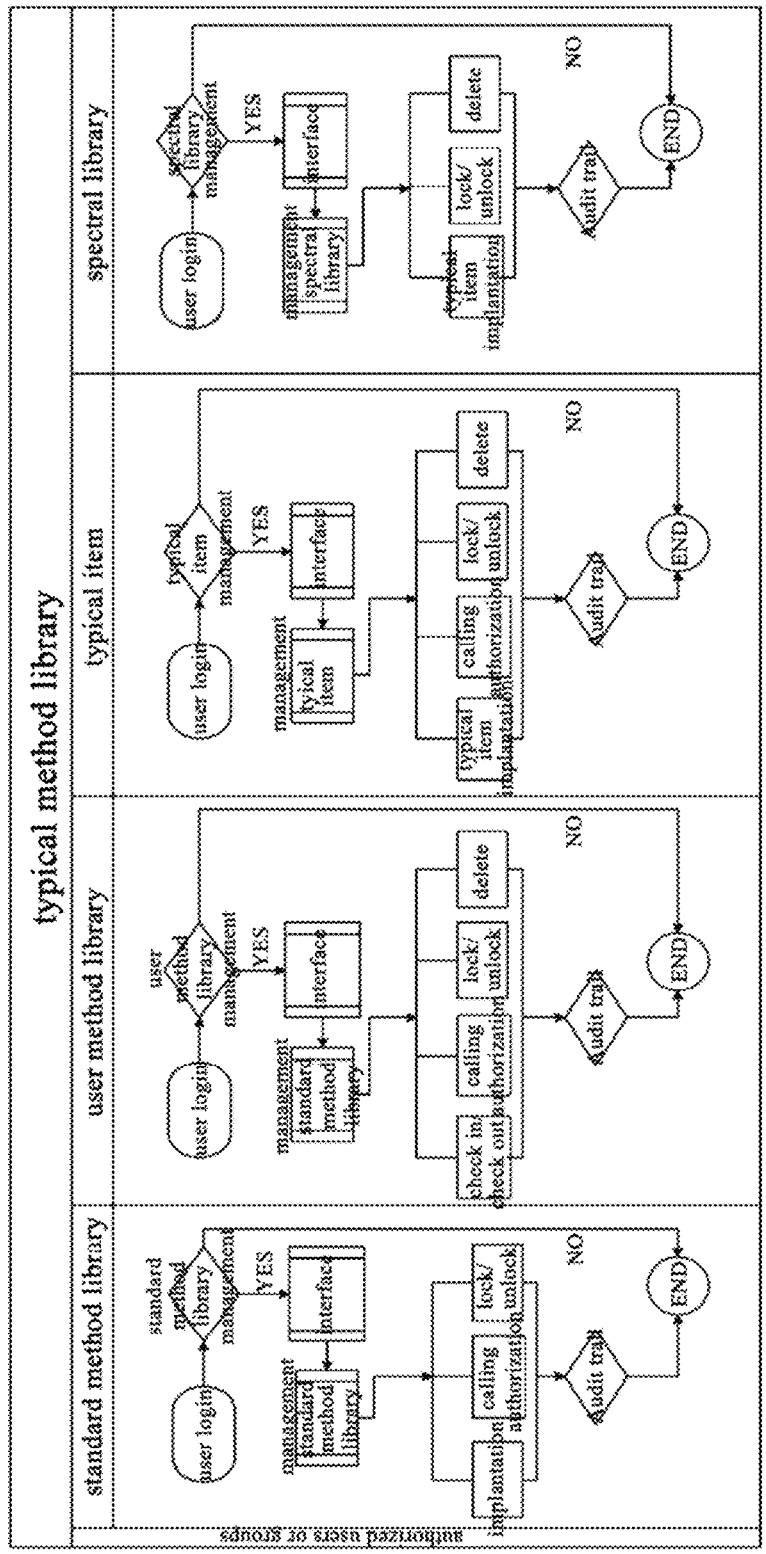
FIG. 5 is a schematic diagram illustrating the functional implementation of a second database managing module according to an embodiment of the application.

For example, FIG. 5 is a schematic diagram illustrating the functional implementation of each specific library of a second database managing module.

Secondly, from the point of view of interaction friendliness and intelligence, although some intelligent auxiliary functions exist in the existing chromatographic software system, such as help files, failure notification, etc., users still need to make judgments according to the specific data displayed by the instrument. In practical use, it is undoubtedly difficult for users who have just come into contact with the instrument. Moreover, the existing chromatographic software system is not intelligent enough in method establishment and method optimization, and it is difficult to guide users to do the next work, no matter whether it is for parameter optimization, method optimization or separation.

In view of this, the chromatographic analysis system in the present disclosure further comprises an intelligent auxiliary unit, wherein the intelligent auxiliary unit comprises an intelligent diagnosis module, and the intelligent diagnosis module is configured to automatically analyze and diagnose instrument faults, generate diagnosis reports and solution suggestions, so as to help users troubleshoot.

The intelligent diagnosis here mainly refers to the automatic troubleshooting of the instrument hardware or faults in the using process of the instrument. In the process of using the instrument, the user needs to monitor the instrument indexes to make sure that there is no problem with the instrument state and ensure the stability of the instrument state. However, there are often some problems to be solved. For example, the instrument cannot be connected in terms of software; for example, the column pressure is too high, the column temperature box fluctuates greatly, and the initial data is difficult to return to zero in terms of instrument performance; for example, lamp energy is too low in terms of consumables. Through intelligent diagnosis, the software system will automatically analyze and diagnose related problems and give solutions after analysis. Operators can follow the prompts to operate and help users solve problems as soon as possible.

For example, intelligent diagnosis can be one-click diagnosis operation. The specific operations are as follows: users and user groups with relevant authorization log in to the interface, and after the conventional method setting, click the intelligent diagnosis system to perform one-click intelligent diagnosis operation.

Figure 6:
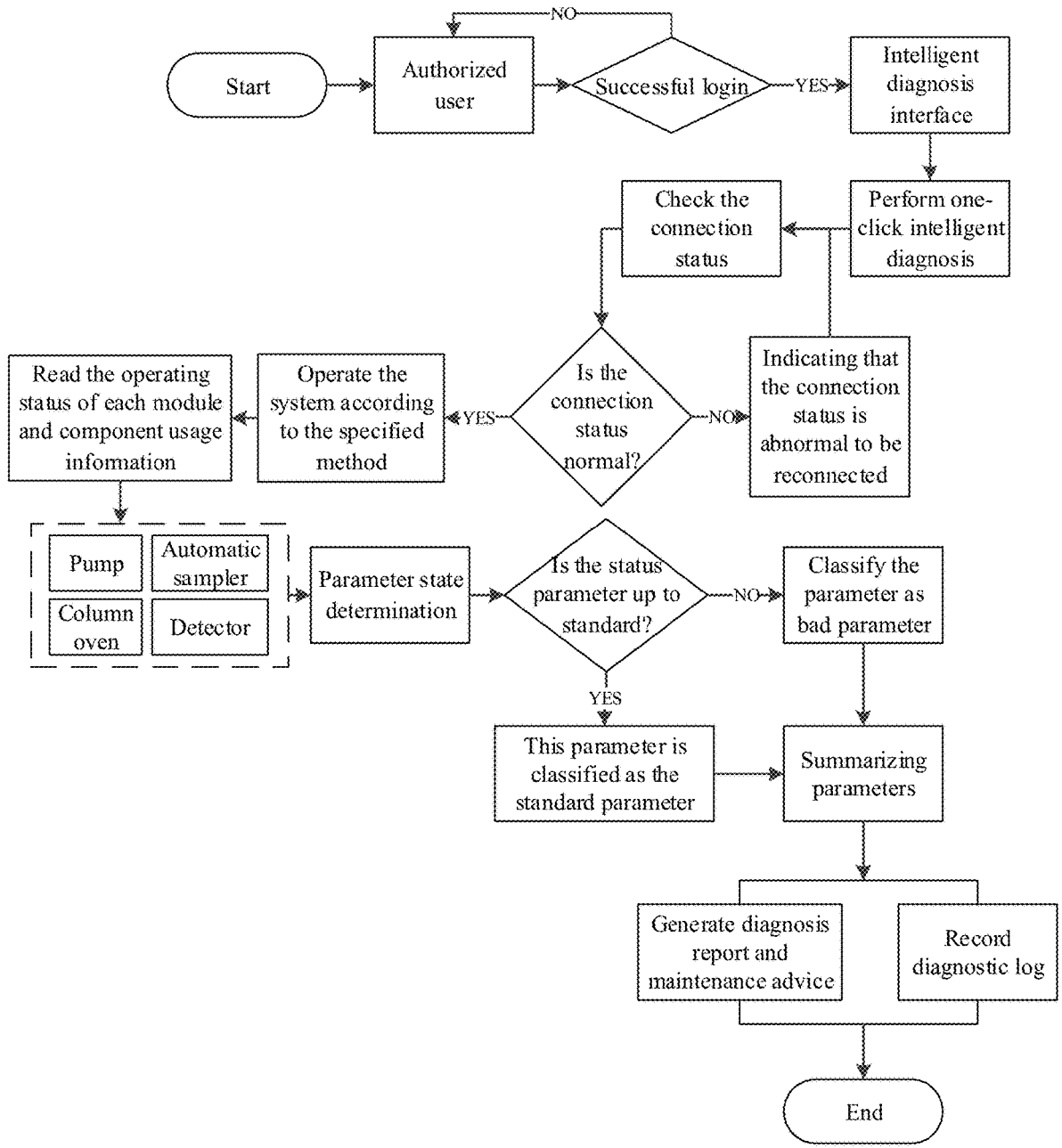
FIG. 6 is a schematic diagram illustrating the functional implementation of an intelligent diagnosis module according to an embodiment of the application.

Specifically, the realization of one-click diagnosis operation mainly involves the judgment after data acquisition and feedback in the process of software controlling instrument hardware. For example, the internal parameters of the instrument are acquired for feedback, and the system judges through the feedback data, and finally gives the diagnosis result. In the implementation, first, the system internally checks the connection state of the instrument, reads the operating state of each module to judge whether the connection state is normal. If the detection is normal, it will continue to operate according to the specified analysis method. Second, it will make parameter judgment, and the system will automatically detect the state of the instrument to judge whether the state parameters are up to standard. If so, the parameters will be classified as the parameters up to standard. If the parameters detected by the system are not up to standard, the parameters will be classified as bad parameters, and the parameters that are up to standard and the parameters that are not up to standard will be summarized, and finally the diagnostic report and diagnostic log will be generated. The realization of this process is shown in FIG. 6.

The intelligent auxiliary unit in the present disclosure further comprises an intelligent chromatographic expert system module; the intelligent chromatographic expert system module is configured to assist users in method development and realize method recommendation and intelligent method matching functions. The chromatographic expert system here refers to a method development "consultant".

Specifically, the intelligent chromatographic expert system module comprises:
   a method intelligent recommendation sub-module, which is configured to perform intelligent diagnosis and parameter recommending on the set method parameters when the user establishes an analysis method; an application knowledge base sub-module, which has the industry standard data, national standards and pharmacopoeia method data used in the industry built therein, and is configured to provide the user with a local knowledge base query function; an intelligent interaction sub-module, which is configured to push a relevant auxiliary prompt to a user when the user performs interactive operation; a gradient method optimization sub-module, which is configured to provide gradient optimization method suggestions to a user when the analysis results are not satisfactory. This is briefly explained hereinafter:

A. Intelligent recommendation of method parameters means that when the user establishes an analysis method, the system will give a certain prompt for the set method according to the settings. Specifically, in practice, after the user sets the method parameters, the system can perform intelligent diagnosis and parameter recommendation on the method parameters set by the customer through the acquisition of information such as instrument system configuration, mobile phase and chromatographic column, provide guidance for the setting of advanced parameters, and give prompts for unreasonable parameter settings, so as to achieve the purpose of avoiding the mis-operation of the customer, improving the working efficiency and accuracy, and reducing the operating cost.

For example, the user first selects the instrument system, and then enters the method setting interface. After the conventional method setting, the user enters the method parameter intelligent recommendation interface in the form of one-click activation. The user selects the functions that need to be diagnosed and recommended according to his own needs. After the function selection, the system will recommend the parameters according to each diagnostic function and give the recommendation and diagnosis results.

B. The application knowledge base sub-module refers to an Off-line application knowledge base (local knowledge base). In practice, relevant personnel will need to consult materials during the detection and analysis operation. The application knowledge base constructs the knowledge base for pharmacopoeia, national standard methods, software use help files, software operation video files, general knowledge of experiments, etc., which is convenient for users to consult and inquire without external network, thus improving efficiency and saving time.

C. The intelligent interaction sub-module involves an On-line interaction function, which is based on the local knowledge base, and gives relevant prompts during the interactive operation of users. Specifically, in the process of using the chromatographic workstation, there are many points and tips that users need to pay attention to, especially for beginners. Therefore, in the process of using chromatographic software, no matter whether it is parameter setting, acquisition management, data processing, etc., it is necessary for the software to intelligently give some prompts.

Based on this demand, in the process of system operation, from the user's point of view, the system will perform intelligent barrage (pop-up prompt box) for the parameters and methods set by users. For example, for chromatographic columns, solvents, methods, parameters, etc., the system intelligently screens the local knowledge base in the background to prompt some tips, knowledge bases, points for attention, etc. For example, when users set the parameters according to their own needs, after selecting the parameters such as separation mode, specific type of chromatographic columns, specific type of mobile phases (assuming that methanol is selected), type of needle washing solution, sampling method, etc., according to these selected method conditions, the system will intelligently give some prompts, such as inappropriate setting of wavelength, inappropriate proportion of mobile phase after selecting the separation mode, etc.

D. The most important purpose of chromatographic software is to control instruments to acquire data, analyze data, and optimize parameters to make data meet requirements and issue reports. The parameter optimization that needs to consume most manpower, material resources and financial resources makes the data meet the analysis requirements. When optimizing the configuration of parameters, it is not only the optimization of instrument parameters, but also the optimization of some external conditions, such as mobile phase (type: whether it contains salt or not, whether acid is added; adjustment of the mobile phase proportion); change of chromatographic columns (length, type, particle size, etc.); change of detecting wavelength, etc. In the process of chromatographic analysis, the detection that meets the requirements cannot be completed after operation according to the initially set parameters. Parameter optimization is often required for many times.

The gradient method optimization sub-module is aimed at this situation. When the analysis results are not satisfactory, suggestions for gradient optimization methods are provided to a user. For example, according to the currently measured spectrogram data and preset logic, the method of using chromatographic columns of a smaller particle size for analysis is recommended to a user.

Embodiment 2

As mentioned in the background, in the existing related technologies for detecting and analyzing chromatograms, a time window method, a derivative method and a pattern matching method have some defects such as good identification of multi-peak overlapping or poor universality.

In view of this, on the basis of Embodiment 1, the present disclosure further proposes a chromatogram detection and analysis method, which detects chromatogram peaks based on pattern matching and in conjunction with the curvature of chromatogram curves. This method is helpful to make up for the defects in the prior art and realize the detection and analysis of chromatogram with better comprehensive performance.

Figure 7:
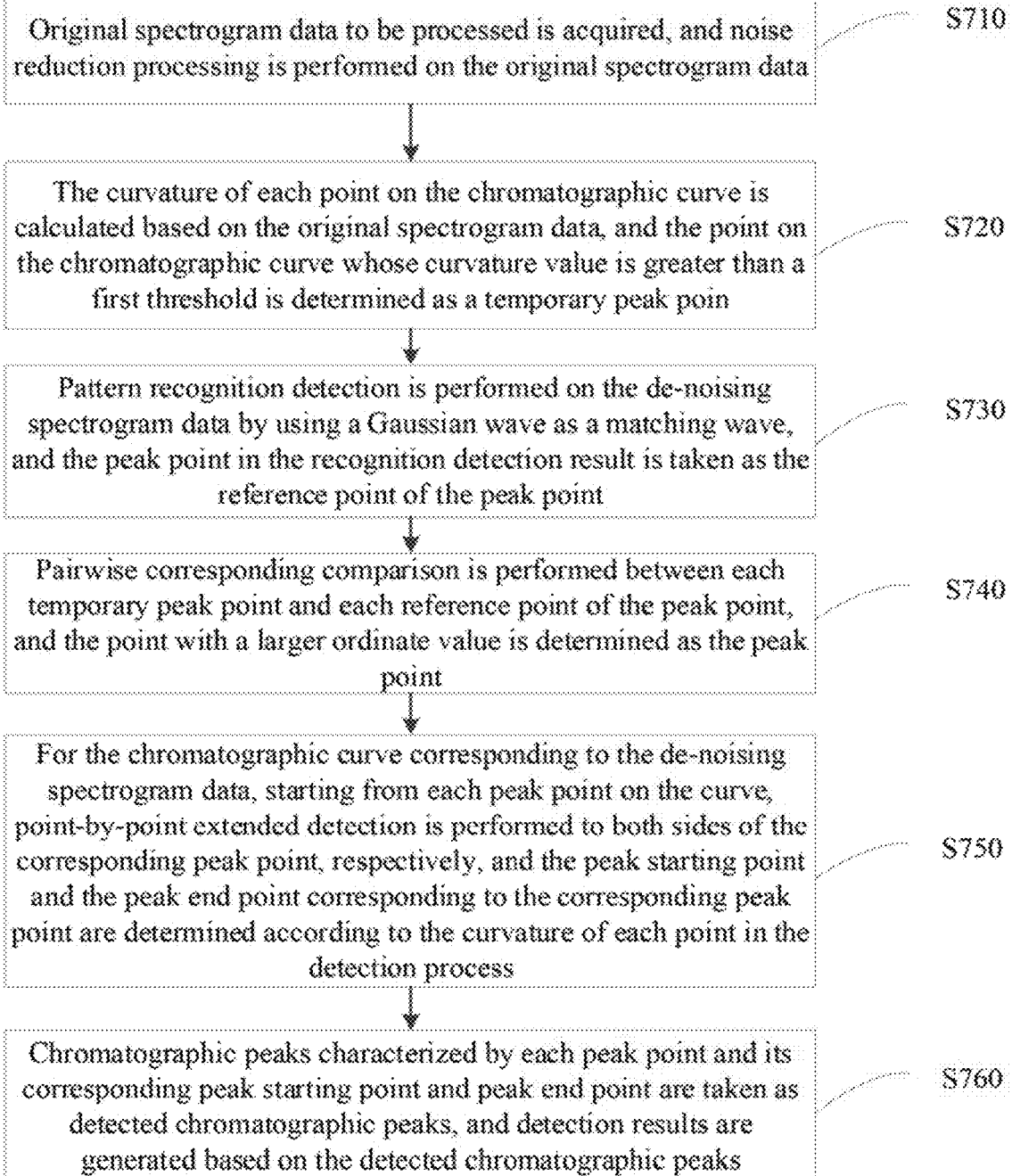
FIG. 7 is a schematic flow diagram of a chromatogram detection and analysis method according to an embodiment of the present disclosure.

As shown in FIG. 7, in one embodiment, the chromatogram detection and analysis method proposed in the present disclosure comprises the following steps.

Step S710, original spectrogram data to be processed is acquired, and noise reduction processing is performed on the original spectrogram data to obtain de-noising spectrogram data.

For example, Savgol_filter filter can be used here to filter the original spectrogram data to remove some noise in the original signal to obtain the de-noising spectrogram data F.

Step S720, the curvature of each point on the chromatographic curve is calculated based on the original spectrogram data, and the point on the chromatographic curve whose curvature value is greater than a first threshold is determined as a temporary peak point, wherein the first threshold is determined based on the calculation and analysis of a no-load output signal of a chromatographic instrument generating the original spectrogram data.

This step is different from the prior art. In the process of detection based on curvature, the threshold is not manually set, but determined based on the calculation and analysis of the no-load output signal of the chromatographic instrument generating the original spectrogram data. Compared with the method of manually setting the threshold, this method has higher reliability, and is beneficial to ensuring the recognition resolution and improving the recognition accuracy.

It is easy for those skilled in the art to understand that, based on the characteristics of spectrogram data, the temporary peak points obtained in step S720 are actually local maximum points of curvature on the chromatographic curve essentially. Generally, for a certain spectrogram data, there are many temporary peak points obtained in step S720.

Step S730, pattern recognition detection is performed on the de-noising spectrogram data by using a Gaussian wave as a matching wave, and the peak point in the recognition detection result is taken as the reference point of the peak point. It is easy to understand that there are many reference points of the peak point here.

After determining the temporary peak points and reference points of the peak point, step S740 is carried out, in which pairwise corresponding comparison is performed between each temporary peak point and each reference point of the peak point, and the point with a larger ordinate value is determined as the peak point.

It is easy to understand that as the detection object is essentially the same spectrogram data, a plurality of temporary peak points obtained in step S720 and a plurality of reference points of the peak point obtained in step S730 have one-to-one correspondence (that is, there are corresponding temporary peak points (x1, y1) and reference points of the peak point (x2, y2) near a certain abscissa horizontal coordinate X).

Pairwise corresponding comparison in step S740 means that for a plurality of temporary peak points and reference points of the peak point, the temporary peak points and reference points of the peak point corresponding to each other are compared. For example, there are corresponding temporary peak points (x1, y1) and reference points of the peak point (x2, y2) near a horizontal coordinate X. The pairwise corresponding comparison in step S740 means that (x1, y1) and (x2, y2) are compared with each other.

After step S740, step S750 is carried out, in which for the chromatographic curve corresponding to the de-noising spectrogram data, starting from each peak point on the curve, point-by-point extended detection is performed to both sides of the corresponding peak point, respectively, and the peak starting point and the peak end point corresponding to the corresponding peak point are determined according to the curvature of each point in the detection process.

It is easy to understand that since the peak point may not be on the curve, the peak point in step S740 refers to the point on the curve corresponding to the horizontal coordinate of the vertex.

Finally, step S760 is carried out, in which chromatographic peaks characterized by each peak point and its corresponding peak starting point and peak end point are taken as detected chromatographic peaks, and detection results are generated based on the detected chromatographic peaks.

Specifically, in step S760, generating the detection result based on the detected chromatographic peak comprises integrating the detected chromatographic peak, and calculating and determining the area and height of the chromatographic peak.

According to the technical scheme of the present disclosure, based on pattern matching and in conjunction with the curvature of the chromatographic curve, the liquid and gas chromatograms are actually detected, which improves the reliability of detection as a whole. In addition, the threshold in the curvature detection method is automatically calculated and determined based on the signal of the instrument itself, and the peak feature points detected by pattern matching are only used as reference points to correct the peak feature points obtained based on curvature detection, which also makes up for the defects of the two methods in the prior art.

For the convenience of understanding the technical scheme of the present disclosure, the technical scheme of the present disclosure will be introduced and explained with another embodiment hereinafter.

In this embodiment, similarly, a first step is performed to acquire the original spectrogram data to be processed, and the original spectrogram data is denoised to obtain denoising spectrogram data F. Then, a second step and a third step are performed.

In the second step, the curvature of each point on the chromatographic curve is calculated based on the original spectrogram data, and the point on the chromatographic curve whose curvature value is greater than a first threshold is determined as a temporary peak point, wherein the first threshold is determined based on the calculation and analysis of a no-load output signal of a chromatographic instrument generating the original spectrogram data.

Specifically, in the second step, the calculation and analysis process of a no-load output signal of a chromatographic instrument generating the original spectrogram data comprises:

performing statistical analysis on the slope change of the output baseline of the chromatographic instrument when it is unloaded, calculating the variance of the slope change, and then determining the standard deviation of the slope change.

In the technical field of analysis instruments, it is generally believed that the slope changes of random noise and baseline drift obey normal distribution and have zero average value. Therefore, we only need to find their variance based on the following expression (1) here.

$$e^2 = \frac{1}{n}\sum_{i=1}^{n} f_i^2 \qquad (1)$$

In expression (1), $e^2$ indicates variance, e indicates standard deviation, $f_i$ indicates the difference between the sample and the average value, and the number n of samples is generally greater than 100.

Furthermore, the standard deviation e of the slope change of a preset multiple is taken as the first threshold $T_{apex}$. In this embodiment, based on the summary of practical engineering experience, as the vertex threshold, the first threshold $T_{apex}$ can be 18 times of the standard deviation e, that is, $T_{apex}=18*e$, so that a better detection effect can be achieved at this time.

In order to obtain the reference point of the peak point, the third step is needed, in which pattern recognition detection is performed on the de-noising spectrogram data by using a Gaussian wave as a matching wave, and the peak point in the recognition detection result is taken as the reference point of the peak point.

Specifically, in this embodiment, pattern recognition detection is performed on the de-noising spectrogram data by using a Gaussian wave as a matching wave, and the peak point in the recognition detection result is taken as the reference point of the peak point. Similar to the prior art, the process comprises:

first, taking the chromatographic curve corresponding to the de-noising spectrogram data F as the curve to be detected, sliding the waveform of the Gaussian wave from the left end point to the right end point on the curve to be detected and simultaneously calculating the correlation coefficients, and obtaining the correlation coefficient group of the chromatographic data of the curve to be detected relative to the Gaussian wave based on the calculation result. The formula of the calculation process is as follows:

$$R = \frac{\sum(x_i - \bar{x})(y_i - \bar{y})}{\sqrt{\sum(x_i - \bar{x})^2 \sum(y_i - \bar{y})^2}} \qquad (2)$$

In expression (2), R indicates the correlation coefficient, $x_i$ and $y_i$ indicate the chromatographic peak data and matched wave data of the current calculated correlation degree, respectively, $\bar{x}$ and $\bar{y}$ indicate the average value of the two groups of data.

Then, each correlation coefficient in the correlation coefficient group is compared and analyzed with a predetermined value, the peak position of the Gaussian wave is determined based on the correlation coefficient whose coefficient value is greater than the predetermined value, and the point at this position on the curve to be detected is determined as the reference point of the peak point.

For example, the predetermined value here is 0.8, and when the correlation coefficient is greater than 0.8, it means that there is a strong correlation therebetween. The process of determining the peak position of the Gaussian wave is the same as that in the prior art, which will not be described in detail here.

After the second step and the third step, a fourth step is carried out, in which pairwise corresponding comparison is performed between each temporary peak point and each reference point of the peak point, and the point with a larger ordinate value is determined as the peak point. This step is similar to the previous embodiment, which will not be described in detail here.

After the fourth step, a fifth step is carried out, in which for the chromatographic curve corresponding to the de-noising spectrogram data, starting from each peak point on the curve, point-by-point extended detection is performed to both sides of the corresponding peak point, respectively, and the peak starting point and the peak end point corresponding to the corresponding peak point are determined according to the curvature of each point in the detection process.

In this embodiment, the point-by-point extended detection here comprises the following processing steps for each peak point:

determining curvature inflection points on both sides of the peak point, specifically, if $S_i$ indicates the curvature of the point i, the point i is considered as the curvature inflection point when $S_{i-1}*S_i<0$ or $S_i=0$;

performing point-by-point detection on the left side with the curvature inflection point on the left side of the peak point as the base point, when the curvature $S_i$ of a point is less than a second threshold $T_{start}$ and the curvature $S_{i-1}$ of the point before the point is greater than the second threshold $T_{start}$ (that is, $S_{i-1}>T_{start}$, $S_i<T_{start}$), comparing the ordinate values of the two points, and determining the point with a smaller ordinate value as the peak starting point corresponding to the peak point, that is, the starting point $\min(F_{i-1}, F_i)$;

similarly, performing point-by-point detection on the right side with the curvature inflection point on the right side of the peak point as the base point, when the curvature $S_i$ of a point is less than a third threshold $T_{end}$ and the curvature $S_{i-1}$ of the point before the point is greater than the third threshold $T_{end}$ (that is, $S_{i-1}>T_{end}$, $S_i>T_{end}$), comparing the ordinate values of the two points, and determining the point with a smaller ordinate value as the peak end point corresponding to the peak point, that is, the end point $\min(F_{i-1}, F_i)$.

It should be noted that in actual implementation, the second threshold $T_{start}$ and the third threshold $T_{end}$ here are configured and determined based on the values input by the user, and their default values are zero when there is no user input.

Finally, a sixth step is carried out, in which chromatographic peaks characterized by each peak point and its corresponding peak starting point and peak end point are taken as detected chromatographic peaks, and detection results are generated based on the detected chromatographic peaks.

Specifically, the detected chromatographic peak is integrated, and the area and height of the chromatographic peak are calculated and determined.

Embodiment 3

As mentioned in the background, in the existing related technologies for detecting and analyzing chromatograms, a time window method, a derivative method and a pattern matching method have some defects such as good identification of multi-peak overlapping or poor universality.

In view of this, on the basis of Embodiment 1, the present disclosure further proposes a chromatogram detection and analysis method, which detects chromatogram peaks based on pattern matching and in conjunction with the slope of chromatogram curves. This method is helpful to make up for the defects in the prior art and realize the detection and analysis of chromatogram with better comprehensive performance.

Figure 8:
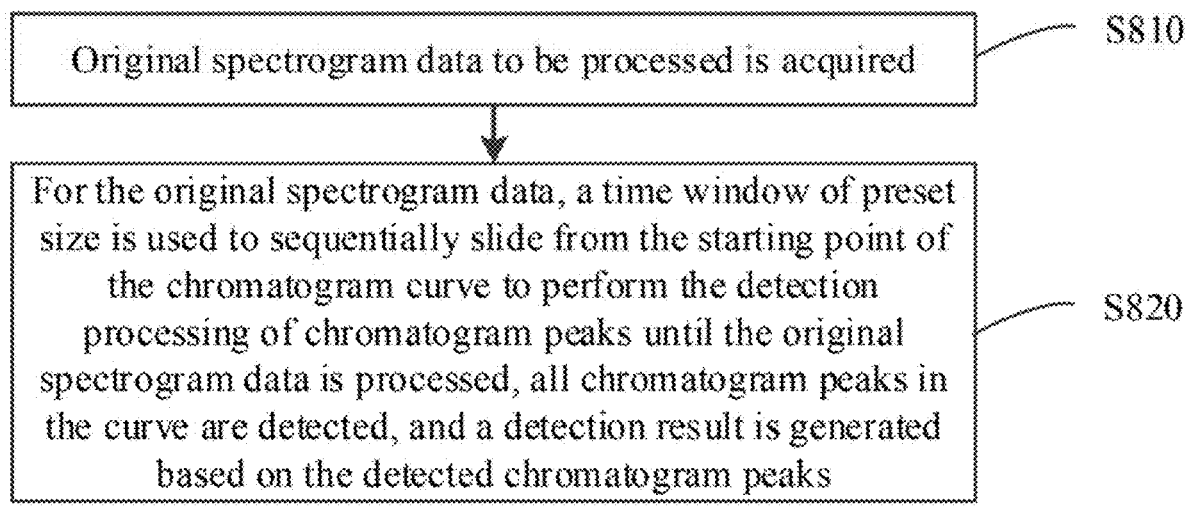
FIG. 8 is another schematic flow diagram of a chromatogram detection and analysis method according to an embodiment of the present disclosure.

As shown in FIG. 8 and FIG. 9, in one embodiment, the chromatogram detection and analysis method proposed in the present disclosure comprises the following steps.

Step S810, original spectrogram data to be processed is acquired.

Step S820, for the original spectrogram data, a time window of preset size (the window size is set based on the standard retention time parameter of the instrument, such as 10% of the standard retention time parameter) is used to sequentially slide from the starting point of the chromatogram curve to perform the detection processing of chromatogram peaks until the original spectrogram data is processed, all chromatogram peaks in the curve are detected, and a detection result is generated based on the detected chromatogram peaks.

It is easy to understand that for a certain complete spectrogram data, there are usually multiple chromatographic peaks, in other words, in the detection process of step S820, each chromatographic peak is detected in sequence by sliding with the time window. Specifically, as shown in FIG. 9, in step S820, the detection process of each chromatographic peak comprises:

step S121, comparing the slope of each point on the chromatographic curve with a threshold, and determining the reference point of the chromatographic peak based on the comparison result, wherein the reference point comprises a reference point of a peak starting point, a reference point of a temporary peak point, and a reference point of a peak end point, and the threshold here is determined based on the calculation and analysis of the no-load output signal of the chromatographic instrument generating the original spectrogram data.

In step S121, unlike the prior art, in the process of detection based on slope, the threshold is not manually set, but determined based on the calculation and analysis of the no-load output signal of the chromatographic instrument generating the original spectrogram data. Compared with the method of manually setting the threshold, this method has higher reliability, and is beneficial to ensuring the recognition resolution and improving the recognition accuracy.

Step S122, based on the position of the chromatographic peak characterized by the reference point on the chromatographic curve, pattern recognition detection is performed on the chromatographic curve near the position with a Gaussian wave as a matching wave, and the peak point in the recognition detection result is taken as the correction point of the peak point.

Step S123, correction processing is performed on the reference point of the temporary peak point according to the correction point of the peak point, and the corrected point is taken as the reference point of the peak point.

Specifically, in this step, by comparing the ordinate values of the correction point of the peak point and the reference point of the temporary peak point, the point with a larger ordinate value is determined as the reference point of the peak point.

Step S124, chromatographic peaks characterized by the reference point of the peak starting point, the reference point of the peak end point and the reference point of the peak point are determined as detected chromatographic peaks.

In step S820, with the sliding of the time window, steps S121-S124 are repeated in each chromatographic peak detection process until all the original spectrogram data are processed.

According to the technical scheme of the present disclosure, based on pattern matching and in conjunction with the slope of the chromatographic curve, the liquid and gas chromatograms are specifically detected actually, which improves the reliability of detection as a whole. In addition, the threshold in the slope detection method is automatically calculated and determined based on the signal of the instrument itself, and the peak feature points detected by pattern matching are only used as reference points to correct the peak feature points obtained based on slope detection, which also makes up for the defects of the two methods in the prior art.

For the convenience of understanding the technical scheme of the present disclosure, the technical scheme of the present disclosure will be introduced and explained with another embodiment hereinafter.

In this embodiment, similarly, a step one is performed to acquire the original spectrogram data to be processed.

Then, a step two is performed, in which for the original spectrogram data, a time window of preset size is used to sequentially slide from the starting point of the chromatogram curve to perform the detection processing of chromatogram peaks until the original spectrogram data is processed, all chromatogram peaks in the curve are detected, and a detection result is generated based on the detected chromatogram peaks.

For example, generating the detection result based on the detected chromatographic peak here comprises integrating the detected chromatographic peak, and calculating and determining the area and height of the chromatographic peak.

Similarly, in this embodiment, in the step two, the detection process of each chromatographic peak comprises:
a step three, comparing the slope of each point on the chromatographic curve with a threshold, and determining the reference point of the chromatographic peak based on the comparison result, wherein the reference point comprises a reference point of a peak starting point, a reference point of a temporary peak point, and a reference point of a peak end point, and the threshold here is determined based on the calculation and analysis of the no-load output signal of the chromatographic instrument generating the original spectrogram data.

Specifically, comparing the slope of each point on the chromatographic curve with a threshold and determining the reference point of the chromatographic peak based on the comparison result comprises:
calculating the slope $G_i$ of the point i on the chromatographic curve in the sliding process of the time window in real time,
comparing the calculated slope $G_i$ with a predetermined fourth threshold $T_{thre}$, comparing the ordinate values of the two points when the slope of two consecutive points is greater than the fourth threshold $T_{thre}$, that is, $G_i > T_{thre}$, $G_{i-1} > T_{thre}$, and determining the point with a smaller ordinate value as the reference point of the peak starting point,
analyzing and judging the positive and negative change of the slope of the point after the reference point of the peak starting point, comparing the ordinate values of the two points when the slope of one point is negative and the slope of the point before the point is positive, that is, for example, $G_{i-1} > 0$, $G_i < 0$, and determining the point with a larger ordinate value as the reference point of the temporary peak point, and
comparing the slope of the point after the reference point of the temporary peak point with a predetermined fifth threshold $T'_{thre}$, comparing the ordinate values of the two points when the slope of two consecutive points is less than the fifth threshold $T'_{thre}$, that is, $G_i < T'_{thre}$, $G_{i-1} < T'_{thre}$, and determining the point with a smaller ordinate value as the reference point of the peak end point.

The fourth threshold $T_{thre}$ and the fifth threshold $T_{thre}$ in the step three are determined based on the calculation and analysis of the no-load output signal of the chromatographic instrument generating the original spectrogram data. The specific determination process is as follows:
performing statistical analysis on the slope change of the output baseline of the chromatographic instrument when it is unloaded, calculating and determining the variance of the slope change, and then determining the standard deviation of the slope change.

In the technical field of analysis instruments, it is generally believed that the slope changes of random noise and baseline drift obey normal distribution and have zero average value. Therefore, we only need to find their variance based on the following expression (3) here.

$$e^2 = \frac{1}{n}\sum_{i=1}^{n} f_i^2 \qquad (3)$$

In expression (3), $e^2$ indicates variance, e indicates standard deviation, $f_i$ indicates the difference between the sample and the average value, and the number n of samples is generally greater than 100.

Then, based on the statistical characteristics of normal distribution (3e can ensure that 97.3% of the baseline slope falls within the zero slope interval), the standard deviation of slope change of three times is taken as the fourth threshold, and the standard deviation of slope change of negative three times is taken as the fifth threshold, that is, the fourth threshold $T_{thre}=3e$ and the fifth threshold $T'_{thre}=-3e$.

After the step three, a step four is performed, in which based on the position of the chromatographic peak characterized by the reference point on the chromatographic curve, pattern recognition detection is performed on the chromatographic curve near the position with a Gaussian wave as a matching wave, and the peak point in the recognition detection result is taken as the correction point of the peak point.

Specifically, in the step four, similar to the prior art, first, the chromatographic curve near this position is taken as the curve to be detected, the waveform of the Gaussian wave slides from the left end point to the right end point on the curve to be detected and the correlation coefficients are simultaneously calculated, and the correlation coefficient group of the chromatographic data of the curve to be detected relative to the Gaussian wave is obtained based on the calculation result. The formula of the calculation process is as follows:

$$R = \frac{\sum(x_i - \bar{x})(y_i - \bar{y})}{\sqrt{\sum(x_i - \bar{x})^2 \sum(y_i - \bar{y})^2}} \qquad (4)$$

In expression (4), R indicates the correlation coefficient, $x_i$ and $y_i$ indicate the chromatographic peak data and matched wave data of the current calculated correlation degree, respectively, $\bar{x}$ and $\bar{y}$ indicate the average value of the two groups of data.

Then, each correlation coefficient in the correlation coefficient group is compared and analyzed with a predetermined value, the peak position of the Gaussian wave is determined based on the correlation coefficient whose coefficient value is greater than the predetermined value, and the point at this position on the curve to be detected is determined as the reference point of the peak point.

For example, the predetermined value here is 0.8, and when the correlation coefficient is greater than 0.8, it means that there is a strong correlation therebetween. The process of determining the peak position of the Gaussian wave is the same as that in the prior art, which will not be described in detail here.

After the step four, a step five is performed, in which by comparing the ordinate values of the correction point of the peak point and the reference point of the temporary peak point, the point with a larger ordinate value is determined as the reference point of the peak point.

In this embodiment, finally, a step six is performed, in which chromatographic peaks characterized by the reference point of the peak starting point, the reference point of the peak end point and the reference point of the peak point are determined as detected chromatographic peaks.

In this embodiment, in the step two, with the sliding of the time window, the steps three to six are repeated in each chromatographic peak detection process until all the original spectrogram data are processed.

According to the technical scheme of the present disclosure, the liquid and gas chromatograms are actually and specifically detected based on pattern matching and in conjunction with the slope of the chromatographic curve. The advantages of the two methods are combined (for example, pattern recognition is insensitive to the changes of noise, chromatographic peak width and amplitude, and has very good anti-interference, fault tolerance and robustness), thereby improving the detection reliability as a whole. In this analysis method, the spectrogram data is identified based on the sliding of time window, which can realize the detection and analysis processing while the spectrogram data is output, so that the detection and analysis results can be output more quickly.

In addition, the threshold in the slope detection method is automatically calculated and determined based on the signal of the instrument itself, and the peak feature points detected by pattern matching are only used as reference points to correct the peak feature points obtained based on curvature detection, which also makes up for the defects of the two methods in the prior art.

In addition, in order to facilitate users to quickly understand and evaluate the performance of the detection and analysis method of the present disclosure, under specific application scenarios, based on the above embodiments 2 and 3, the technical scheme of the present disclosure further comprises:

Detection processing is performed on the original spectrogram data using a reference chromatogram detection algorithm to obtain a reference detection result; the detection result is compared and analyzed with the reference detection result, a detection evaluation report is generated, and the detection evaluation report is displayed and output. The reference chromatogram detection algorithm here refers to other detection and analysis methods except the detection and analysis method of the present disclosure, which achieve the same functional purpose as the method of the present disclosure.

Figure 10:
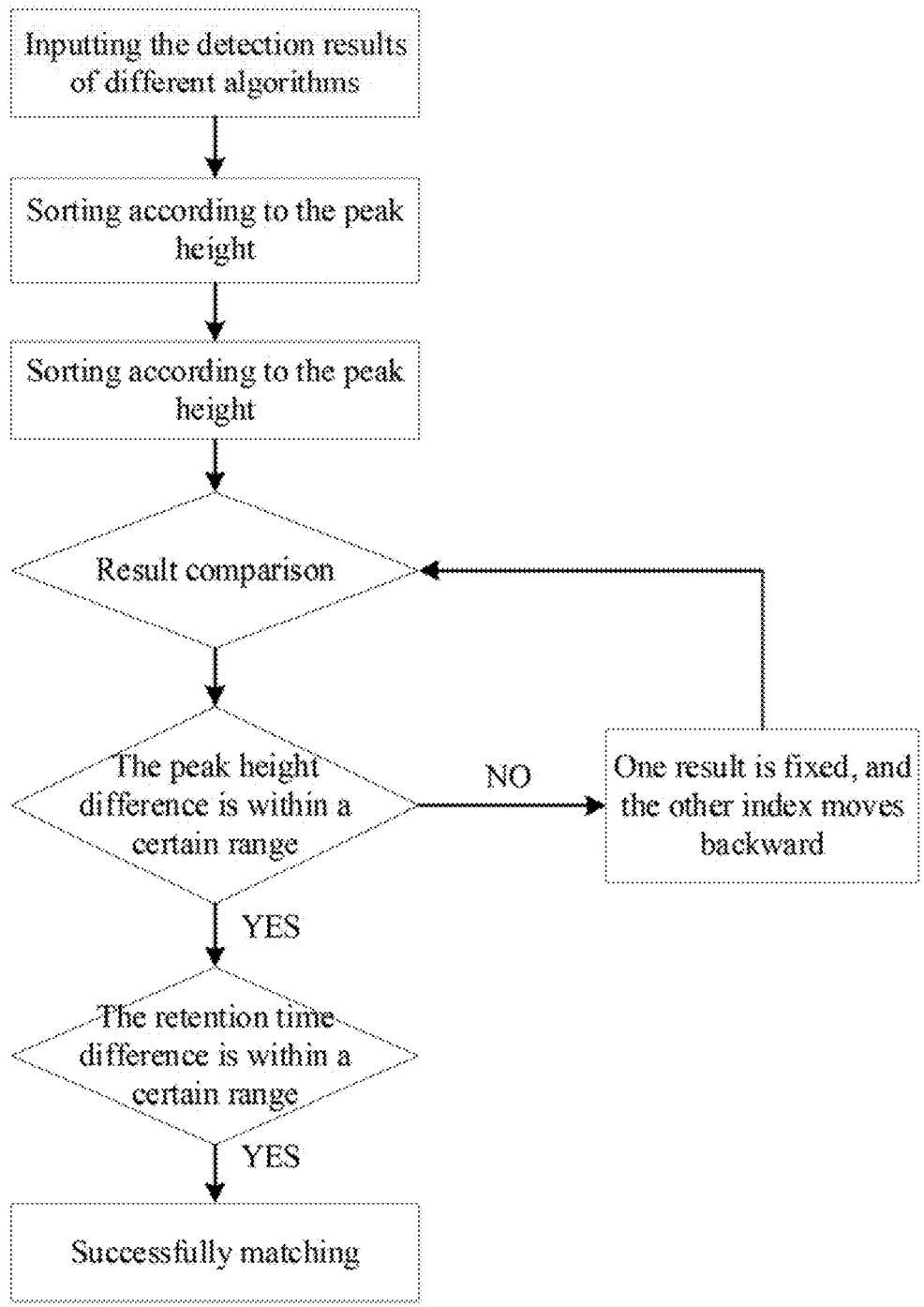
FIG. 10 is a schematic diagram of the implementation flow of the chromatographic peak matching between different detection results according to an embodiment of the present disclosure.
Figure 11:
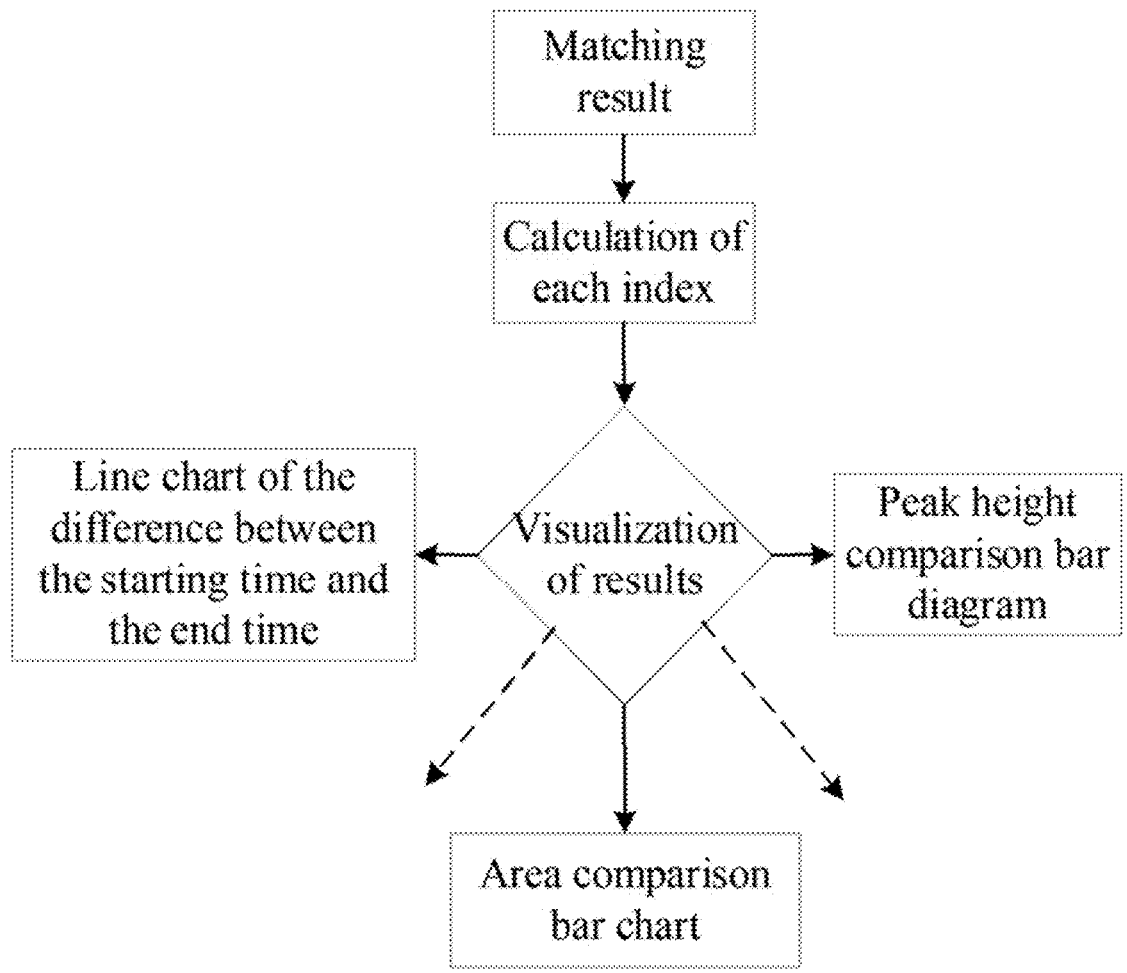
FIG. 11 is a schematic diagram of the implementation flow of the display and output of the detection and evaluation report according to an embodiment of the present disclosure.

Comparing and analyzing the detection result with the reference detection result comprises: matching the detected chromatographic peaks in the detection result and the reference detection result, determining the matched chromatographic peaks (the flow process is shown in FIG. 10), and generating a detection evaluation report based on the proportion of the matched chromatographic peaks in the detected chromatographic peaks and the difference of the matched chromatographic peaks (the flow process is shown in FIG. 11).

In other words, in the evaluation and analysis process of the present disclosure, instead of comparing the results in one-to-one correspondence from the time series, the results of the detected peaks are first ranked in descending order according to the peak height, wherein the peak results include the peak starting point, the peak end point, the peak height, the area, the retention time (the corresponding time of the peak point), the starting point of the baseline and the end point of the baseline, and then the ranked results are compared and matched (one peak result corresponds to one piece of data, and the whole data will follow the peak height).

As shown in FIG. 10, in this implementation, first, the dual conditions of peak height and retention time are considered for comparison and matching. First, the peak heights are compared. If the difference between the peak heights of the comparison algorithm is within a certain range, the retention time is compared. If the difference is within a certain range, it means that the corresponding peak of the comparison algorithm can be correspondingly matched, and the comparison results are saved for subsequent calculation of their index values.

If either of the two conditions is not met, it is considered that the current comparison data are not matched, one index is fixed, and the other result index moves backward until the data that can be matched or the other data index moves to the last data. It is worth noting that the calculation results of different algorithms for the same peak of the same chromatographic data are not necessarily identical. Because of the difference of algorithms, there are some differences in the results, but the difference value is not very large, so that the difference value is within a certain range. Of course, there may be similar peak heights in the same chromatographic data. Therefore, when comparing the results, the present disclosure will also increase the comparison of retention time according to the corresponding situation to ensure the accuracy of the results.

After the matching process is completed, the matched peak result information is stored in one-to-one correspondence, and then the corresponding index is calculated according to the result information of each peak, turning to the visual output stage of detection and evaluation report shown in FIG. 11. Specifically, the detection and evaluation report in this stage comprises the following steps.

A. Checking the approximate matching results

The number of matched peaks and unmatched peaks is plotted for visual display, for example, using a bar chart for display. Assuming that the number of peaks detected by method1 (detection and analysis method of the present disclosure) is n, the number of peaks detected by method2 (refer to the chromatogram detection algorithm) is m, and the number of matched peaks is s, where s<min(n,m). A histogram consists of three parts. The lower part is the number n-s of unmatched peaks in method1, the middle part is the number of matched peaks s of two algorithms, and the upper part is the number m-s of unmatched peaks in method2. If the proportion of the middle part is relatively large, it means that the number of peaks detected by the two algorithms is relatively large and the detection performance is relatively close.

B. In most cases, chromatographic data will produce some noise due to instrument and experimental conditions, and different algorithms have different sensitivity to noise. When matching, small peaks are often not matched. However, to a certain extent, this situation will mislead the results obtained in A described above. Therefore, a comparative bar chart is added here, in which the percentage of the total area $$\sum_{i=1}^{s} area_i$$

of the matched peak to the total area $$\sum_{i=1}^{n} area_i, \sum_{i=1}^{m} area_i$$

of all peaks is $$\sum_{i=1}^{s} area_i / \sum_{i=1}^{m} area_i, \sum_{i=1}^{s} area_i / \sum_{i=1}^{n} area_i.$$

If the two percentage results are very close and the values are relatively large, it is considered that the big peaks of the two groups of results are matched, which verifies the difference of the detection performance of the two algorithms from another index.

C. Checking whether the matching result is abnormal.

Specifically, for example, the std (root mean square error) of the difference between the starting point and the end point of the matched peak is calculated, respectively. if std of the difference of peak areas floats within a certain range, then it is considered that there is no obvious abnormality at the starting point and the end point of the peaks matched by the two comparison algorithms. Otherwise, it is considered that there is an abnormal point, and then we can find out what kind of abnormality occurs in the detection algorithm according to the abnormal data.

Furthermore, it is easy to understand that for different raw data, the algorithm is compared and analyzed based on the corresponding results. One data can correspond to an evaluation report. A comprehensive evaluation of the overall data results is formed according to these reports to comprehensively evaluate the performance of the algorithm.

Based on the spectrogram data in embodiment 1, embodiment 2 and embodiment 3, it can be seen that the data processing of the chromatogram can be realized in embodiment 1, embodiment 2 and embodiment 3 of the present disclosure, so as to achieve the technical effects of ensuring the integrity and security of the acquired raw data.

Figure 12:
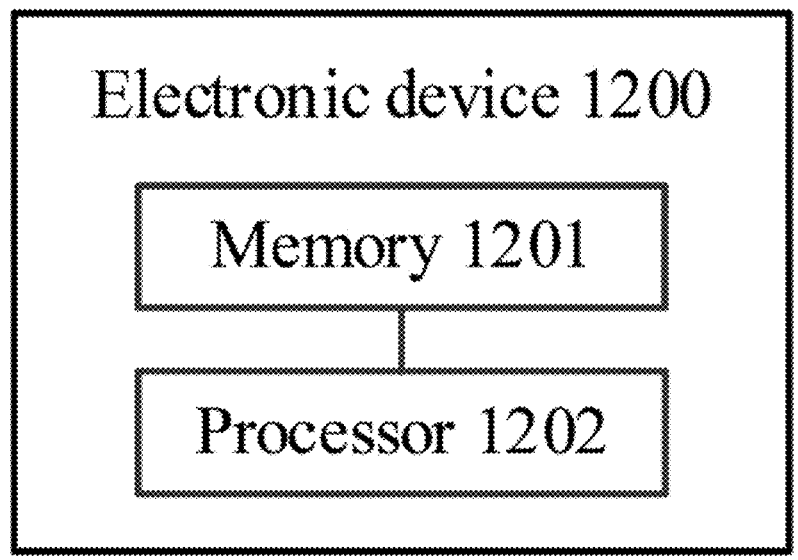
FIG. 12 is a structural diagram of an electronic device according to an embodiment of the present disclosure.

FIG. 12 is a schematic structural diagram of an electronic device according to an embodiment of the present disclosure. As shown in FIG. 12, the electronic device 1200 comprises:

a memory 1201 on which an executable program is stored;

a processor 1202 which is configured to execute the executable program in the memory to realize the steps of the method described above.

As for the electronic device 1200 in the above embodiment, the specific way in which the processor 1202 executes the program in the memory 1201 has been described in detail in the embodiment related to this method, which will not be explained in detail here.

The above is only the preferred embodiment of the present disclosure, but the scope of protection of the present disclosure is not limited thereto. Any changes or substitutions that can be easily conceivable to those skilled in the art within the technical scope disclosed by the present disclosure should fall within the scope of protection of the present disclosure. Therefore, the scope of protection of the present disclosure should be subject to the scope of protection of the claims.

What is claimed is:

1. A chromatographic analysis system based on a dual-database architecture, comprising:
    a data acquiring unit, which is configured to acquire raw data generated by a chromatographic analysis instrument;
    an analysis processing unit, which is configured to analyze the raw data based on an analysis operation configured by a user to obtain analysis data;
    a storing and managing unit, which is configured to store raw data and analysis data, and store method parameters and management data of the analysis system; and
    a client unit, which is configured to provide an interactive interface of the system to the user;
    wherein the storing and managing unit comprises a first database configured for storing raw data and analysis data and a second database configured for storing method parameters and management data of the analysis system;
    wherein a method library, a item library and a user method library are built in the second database;
    the method library integrates a plurality of traditional Chinese medicine analysis methods, which are established based on the separation requirements and a content analysis method of corresponding traditional Chinese medicine in pharmacopoeia;
    the item library is configured to store used detection items in the field, and the detection items comprise analysis methods and spectrogram data corresponding to corresponding items; and
    the user method library is configured to store the analysis methods established by the user, which facilitates the reuse of the analysis methods;
    wherein the storing and managing unit further comprises a second database managing module;
    the second database managing module is configured to realize an implantation and deletion function, an authorization management function, an item locking and unlocking function, and a check-in and check-out function of online users of items.

2. The chromatographic analysis system according to claim 1, wherein the item library stores one-click detection items; and
    sample configuration requirements, instruments and operation requirements, analysis method configuration and analysis report templates are built in the one-click detection items, which is convenient for the user to call the item for one-click detection and analysis operation through the interactive interface.

3. The chromatographic analysis system according to claim 1, further comprising an intelligent auxiliary unit, wherein the intelligent auxiliary unit comprises an intelligent diagnosis module;
    the intelligent diagnosis module is configured to automatically analyze and diagnose instrument faults, generate diagnosis reports and solution suggestions, so as to help users troubleshoot.

4. The chromatographic analysis system according to claim 3, wherein the intelligent auxiliary unit further comprises an intelligent chromatographic expert system module;

the intelligent chromatographic expert system module is configured to assist users in method development and realize method recommendation and intelligent method matching functions.

5. The chromatographic analysis system according to claim 1, further comprising a Web server unit, which is configured to provide the interactive interface of the system to the user in the form of browser pages.

6. The chromatographic analysis system according to claim 1, wherein both the first database and the second database are deployed in the cloud.

7. A chromatographic analysis system based on a dual-database architecture, comprising:
- a data acquiring unit, which is configured to acquire raw data generated by a chromatographic analysis instrument;
- an analysis processing unit, which is configured to analyze the raw data based on the analysis operation configured by a user to obtain analysis data;
- a storing and managing unit, which is configured to store raw data and analysis data, and store method parameters and management data of the analysis system;
- a client unit, which is configured to provide the interactive interface of the system to the user;
- an intelligent auxiliary unit, wherein the intelligent auxiliary unit comprises an intelligent diagnosis module, and the intelligent diagnosis module is configured to automatically analyze and diagnose instrument faults, generate diagnosis reports and solution suggestions, so as to help users troubleshoot wherein the storing and managing unit comprises a first database for storing raw data and analysis data and a second database for storing method parameters and management data of the analysis system;

wherein the intelligent auxiliary unit further comprises an intelligent chromatographic expert system module, and the intelligent chromatographic expert system module is configured to assist users in method development and realize method recommendation and intelligent method matching functions;

wherein the intelligent chromatographic expert system module comprises:
- a method intelligent recommendation sub-module, which is configured to perform intelligent diagnosis and parameter recommending on a set method parameters when the user establishes an analysis method;
- an application knowledge base sub-module, which has an industry standard data, national standards and pharmacopoeia method data used in an industry built therein, and is configured to provide the user with a local knowledge base query function;
- an intelligent interaction sub-module, which is configured to push a relevant auxiliary prompt to the user when the user performs interactive operation;
- a gradient method optimization sub-module, which is configured to provide gradient optimization method suggestions to the user when an analysis results are not satisfactory.

* * * * *